(12) United States Patent
Pecherer

(10) Patent No.: US 10,849,488 B2
(45) Date of Patent: Dec. 1, 2020

(54) LARYNGOSCOPE HANDLE AND RETROFITTABLE INSUFFLATION MODULE THEREFOR

(71) Applicant: Evgeny Pecherer, Netanya (IL)

(72) Inventor: Evgeny Pecherer, Netanya (IL)

(*) Notice: Subject to any disclaimer, the term of this patent is extended or adjusted under 35 U.S.C. 154(b) by 430 days.

(21) Appl. No.: 15/978,234

(22) Filed: May 14, 2018

(65) Prior Publication Data
US 2018/0279867 A1    Oct. 4, 2018

Related U.S. Application Data

(63) Continuation-in-part of application No. 14/917,580, filed as application No. PCT/IB2014/064396 on Sep. 10, 2014, now Pat. No. 9,968,248.

(60) Provisional application No. 62/505,924, filed on May 14, 2017, provisional application No. 61/876,779, filed on Sep. 12, 2013.

(51) Int. Cl.
| | |
|---|---|
| *A61B 1/267* | (2006.01) |
| *A61B 1/00* | (2006.01) |
| *A61B 1/015* | (2006.01) |
| *A61B 1/12* | (2006.01) |
| *A61B 1/012* | (2006.01) |

(52) U.S. Cl.
CPC .......... *A61B 1/267* (2013.01); *A61B 1/00066* (2013.01); *A61B 1/00091* (2013.01); *A61B 1/00105* (2013.01); *A61B 1/012* (2013.01); *A61B 1/015* (2013.01); *A61B 1/127* (2013.01); *A61B 1/00121* (2013.01)

(58) Field of Classification Search
CPC .......... A61B 1/267; A61B 1/015; A61B 1/012
See application file for complete search history.

(56) References Cited

U.S. PATENT DOCUMENTS

| | | | | |
|---|---|---|---|---|
| 4,037,588 A | * | 7/1977 | Heckele | A61B 1/267 600/191 |
| 5,349,943 A | * | 9/1994 | Ruiz | A61B 1/267 600/189 |
| 5,702,351 A | * | 12/1997 | Bar-Or | A61B 1/267 600/185 |
| 6,106,458 A | | 8/2000 | Ha | |
| 2003/0092967 A1 | | 5/2003 | Fourie et al. | |
| 2007/0161863 A1 | | 7/2007 | Bentt | |
| 2008/0051628 A1 | * | 2/2008 | Pecherer | A61B 1/267 600/112 |
| 2008/0177147 A1 | * | 7/2008 | Simons | A61B 1/267 600/186 |

(Continued)

FOREIGN PATENT DOCUMENTS

FR    2746626 A1    10/1997

*Primary Examiner* — Christian A Sevilla
(74) *Attorney, Agent, or Firm* — AlphaPatent Associates, Ltd; Daniel J. Swirsky

(57) ABSTRACT

A laryngoscope handle has a lower grip and an upper functional portion comprising a blade-retention portion formed with a slot extending in a longitudinal direction parallel to a viewing axis, and being configured for slidingly receiving therewithin a laryngoscope blade, and a module-coupling mechanism. An insufflation module may include a body; a jet nozzle extending from the body, the jet nozzle configured and operable to deliver a high velocity stream of gas in a direction substantially along a blade of the laryngoscope such that the gas is deliverable into an intraoral cavity.

11 Claims, 12 Drawing Sheets

(56) References Cited

U.S. PATENT DOCUMENTS

| | | |
|---|---|---|
| 2008/0242941 A1 | 10/2008 | Kim et al. |
| 2009/0099421 A1 | 4/2009 | Shalman et al. |
| 2010/0121152 A1 | 5/2010 | Boedeker |
| 2016/0089002 A1* | 3/2016 | Burton .................. A61B 1/015 |
| | | 600/154 |

* cited by examiner

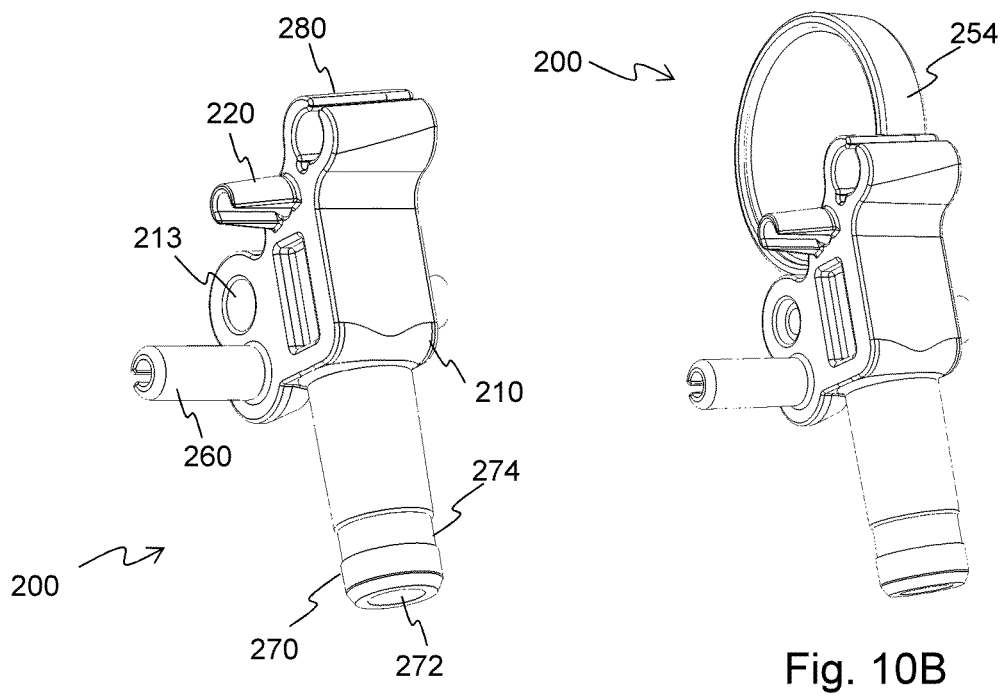
Fig. 10A
Fig. 10B
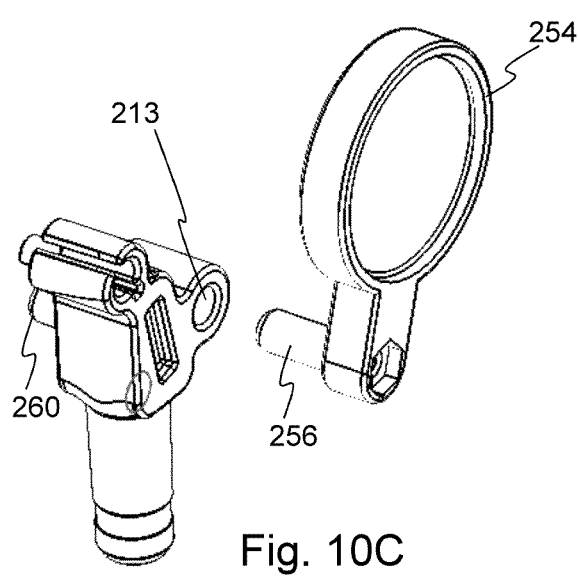
Fig. 10C

LARYNGOSCOPE HANDLE AND RETROFITTABLE INSUFFLATION MODULE THEREFOR

This application claims the benefit of priority from U.S. Provisional Application No. 62/505,924, filed May 14, 2017, and is a Continuation-In-Part of U.S. patent application Ser. No. 14/917,580, filed Sep. 10, 2014, and issued as U.S. Pat. No. 9,968,248 on May 15, 2018, which is a U.S. National Phase Application under 35 U.S.C. 371 of International Patent Application No. PCT/IB2014/064396, filed Sep. 10, 2014, which claims the benefit of priority from U.S. Provisional Application No. 61/876,779, filed Sep. 12, 2013, the contents of all of which are incorporated by reference in their entirety.

FIELD

The present disclosure relates to laryngoscopes and laryngoscope handles, especially those designed for use with infants and neonates. In particular the disclosure relates to retrofittable insufflation modules which may be attached to a laryngoscope handle to provide additional functionality.

BACKGROUND

Endotracheal tubes are utilized in a wide variety of medical procedures to provide an unobstructed air passage to a patient's trachea. In order to facilitate insertion of an endotracheal tube into a patient's airway, a laryngoscope may be used.

A laryngoscope typically comprises a blade, along which the endotracheal tube is guided, and a handle, which is manipulated to alter the position of the blade within the patient's airway. In addition, other features, such as lights, etc., may be provided.

US 2003/0092967 discloses a laryngoscope comprising a handle having an axis and carrying a light source of a type having an axis extending in the general direction in which a light beam is emitted thereby is described. The laryngoscope has a removable and replaceable, preferably disposable, blade of translucent material carried by the handle and extending generally transversely relative to the handle axis. The blade has a proximal end and a distal end, and the light source is directed transversely relative to the axis of the handle so as to aim the light beam directly at, and generally at right angles to, a transverse light receiving face formed at the proximal end of the blade. A light focusing "lens" may be interposed between the light source and the transverse light receiving face. The handle is preferably made of molded plastics material and is ergonomically contoured to form a grip which is comfortable to hold; easy for a medical practitioner to position; and which can be effectively gripped.

SUMMARY

In one aspect of the current disclosure an insufflation module is described for providing insufflation functionality to a laryngoscope. The insufflation module may include a body; a jet nozzle extending from the body, the jet nozzle configured and operable to deliver a high velocity stream of gas in a direction substantially along a blade of the laryngoscope such that the gas is deliverable into an intraoral cavity; an inlet pipe connector configured to connect the body to a gas delivery pipe; a gas inlet via which the gas may be introduced. The insufflation module further includes a gas duct extending from the gas inlet to the jet nozzle through the body of the insufflation module, the gas duct comprising a neck portion and a throat portion. The neck portion has a decreasing cross section tapering towards the throat portion such that when a pressurized gas stream is introduced via the gas inlet the flow-rate of the gas stream increases as the gas stream flows through the duct. The throat portion terminates in a narrow opening of the nozzle such that the gas stream issues from the jet nozzle at a high velocity.

The insufflation module may also include a laryngoscope-coupling mechanism configured to engage with a corresponding module-coupling mechanism of a laryngoscope such that the insufflation module is securely fastened thereto.

Optionally, the laryngoscope coupling mechanism comprises a coupling pin and the corresponding module-coupling mechanism comprises a socket configured to rotatably engage the coupling pin.

Where appropriate, the insufflation module may further include at least one additional module coupling mechanism for connecting further modules thereto. The module coupling mechanism may comprise a lens-mount coupling mechanism comprising a socket configured to rotatably engage a coupling pin of a lens-mount. Optionally, the additional module-coupling mechanism has similar dimensions to the corresponding module-coupling mechanism of the laryngoscope.\

Additionally or alternatively, the insufflation module may further include an auxiliary tube attachment dock configured to secure an auxiliary tube such that the auxiliary tube extends along the line or the laryngoscope blade. Optionally, the auxiliary tube may extend along the line or the laryngoscope blade.

Where required, the insufflation module may include a magnifying lens alignable along a viewing axis of the laryngoscope.

Optionally, the throat portion of the gas duct comprises a bend directing the gas stream towards the jet nozzle, which may have an angle within the range 80 and 100 degrees. Optionally the inlet pipe connector comprises a narrow waist configured to anchor a flexible pipe secured thereby.

In another aspect of the disclosure a laryngoscope handle is described comprising a lower grip and an upper functional portion, the functional portion comprising a blade-retention portion formed with a slot extending in a longitudinal direction parallel to a viewing axis, and being configured for slidingly receiving therewithin a laryngoscope blade; and a module-coupling mechanism configured to engage with a corresponding module coupling mechanism of at least one retrofittable extension module. Optionally, the module-coupling mechanism may comprise a socket configured to engage a coupling pin of the retrofittable extension module. Additionally or alternatively, the module-coupling mechanism comprises a coupling pin configured to engage a socket of the retrofittable extension module.

Where required, the module-coupling mechanism may be configured to securely engage the extension module to the laryngoscope handle allowing rotation movement around its central axis and preventing lateral movement along its length.

BRIEF DESCRIPTION OF THE DRAWINGS

For a better understanding of the embodiments and to show how it may be carried into effect, reference will now be made, purely by way of example, to the accompanying drawings.

With specific reference now to the drawings in detail, it is stressed that the particulars shown are by way of example and for purposes of illustrative discussion of selected embodiments only, and are presented in the cause of providing what is believed to be the most useful and readily understood description of the principles and conceptual aspects. In this regard, no attempt is made to show structural details in more detail than is necessary for a fundamental understanding; the description taken with the drawings making apparent to those skilled in the art how the several selected embodiments may be put into practice. In the accompanying drawings:

FIG. 10A is a perspective view of a retrofittable insufflation module for a laryngoscope handle according to the presently disclosed subject matter;

FIG. 10B is another perspective view of the retrofittable insufflation module for a laryngoscope handle upon which a magnifying lens has been mounted;

FIG. 10C is an exploded view of the retrofittable insufflation module and the lens mount;

DETAILED DESCRIPTION

Figure 1A:
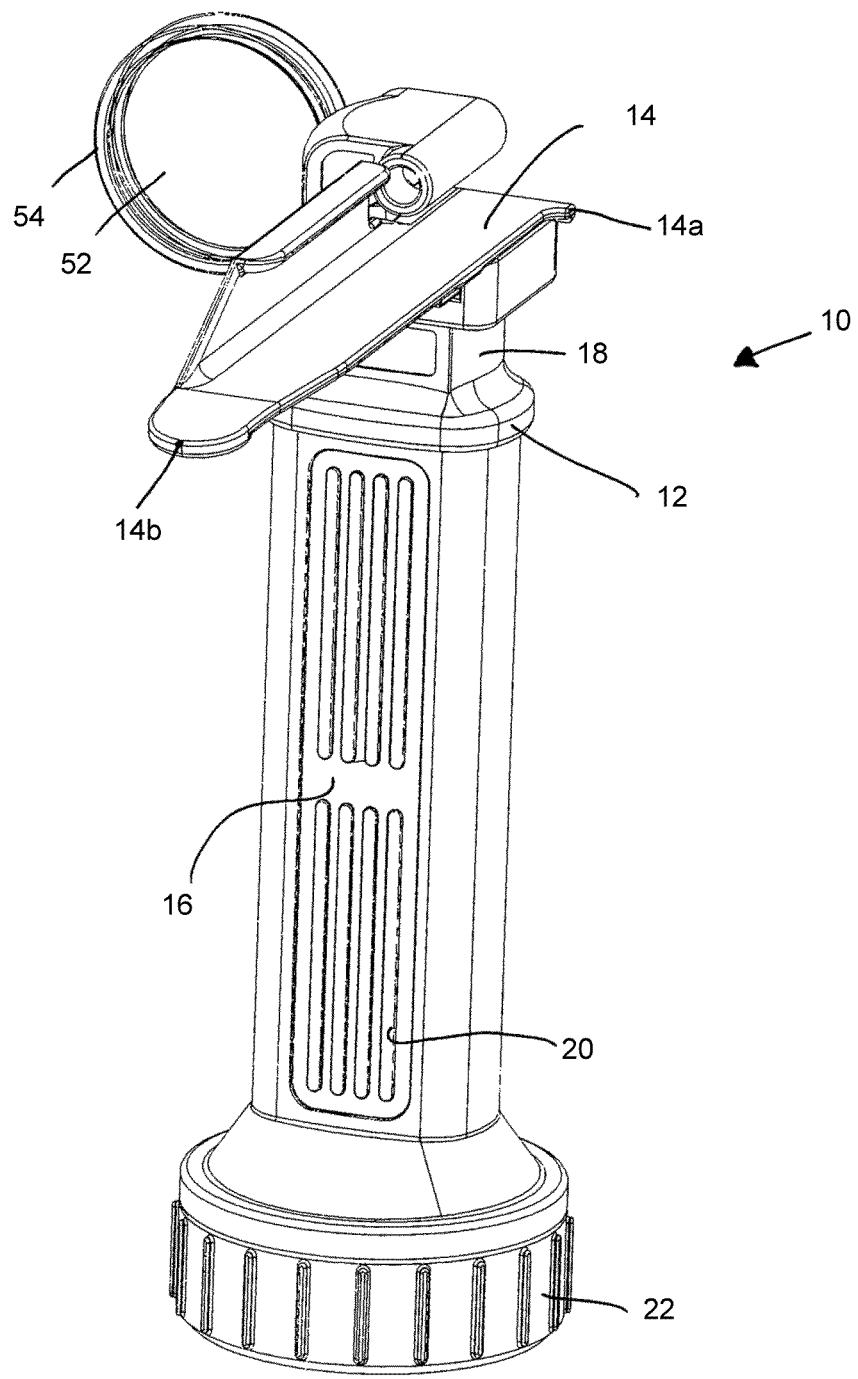
FIGS. 1A and 1B are perspective views of a laryngoscope according to examples of the presently disclosed subject matter.
Figure 1B:
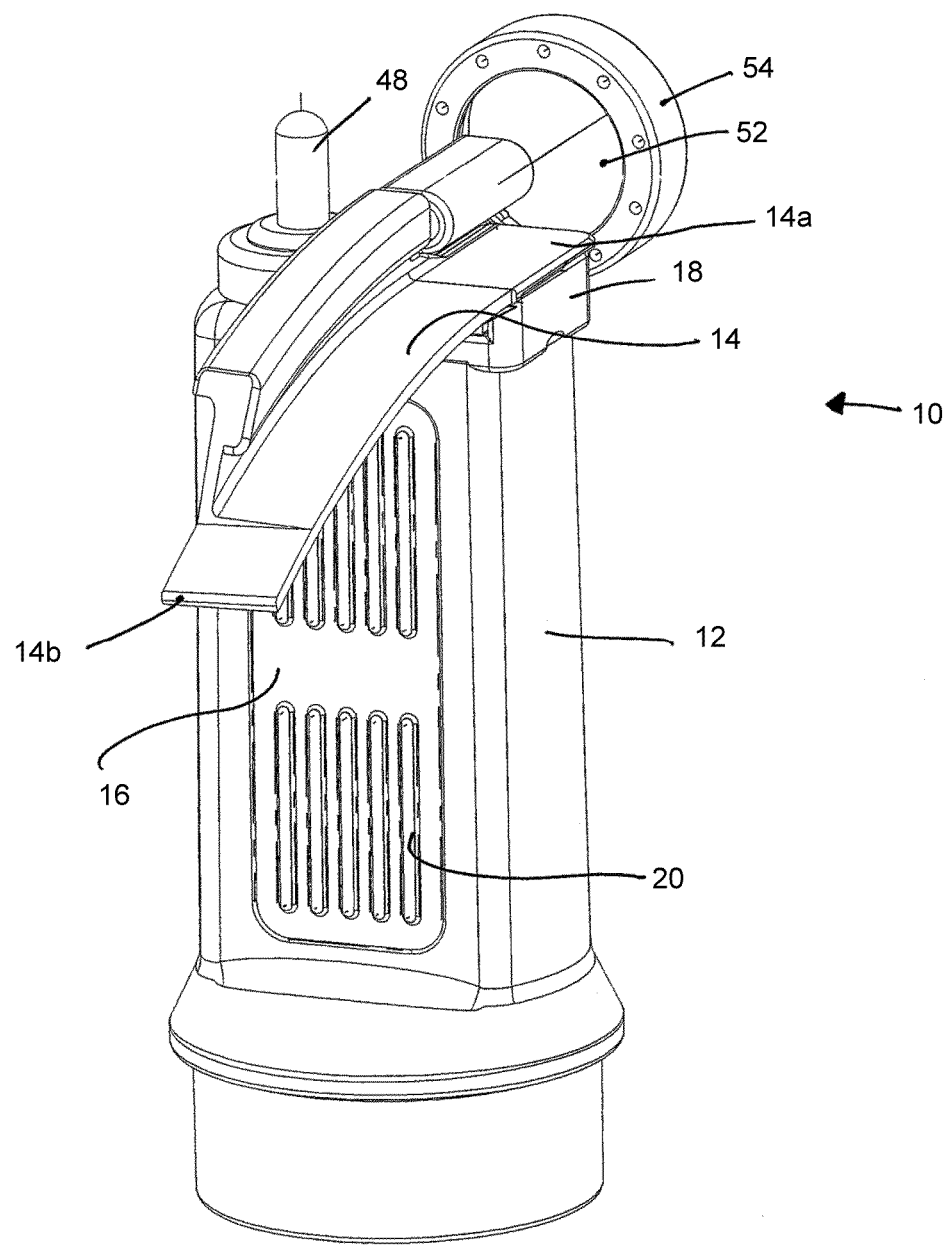

As illustrated in FIGS. 1A and 1B, there is provided a laryngoscope, which is generally indicated at 10, according to the presently disclosed subject matter. The laryngoscope 10 comprises a handle 12 and a blade 14, attached at a proximal end 14a thereof to the handle and which may be removable.

The handle 12 comprises a grip 16, constituting a lower section thereof, and a functional portion 18, constituting an upper portion thereof. It will be appreciated that herein the specification and claims, the terms "upper" and "lower", as well as related terms (such as "up", "down", etc.) are to be understood according to the orientation of the laryngoscope illustrated in FIGS. 1A and 1B, and not according to the orientation than a laryngoscope may be during use.

The grip 16 is constructed so as to facilitate being grasped comfortably and securely by a user performing an intubation procedure with the laryngoscope 10. As such, it may be formed with a plurality of ribs 20, and/or any other suitable feature, such as arcuate indentations (not illustrated) formed to accommodate a user's fingers while grasping the grip 16, etc. IT may be made of any suitable material, such as plastic, an elastomer, etc. In addition, it may be made of more than one material. For example, it may be made primarily of plastic, with some parts thereof, such as the ribs 20, being made of an elastomeric material.

Figure 2:
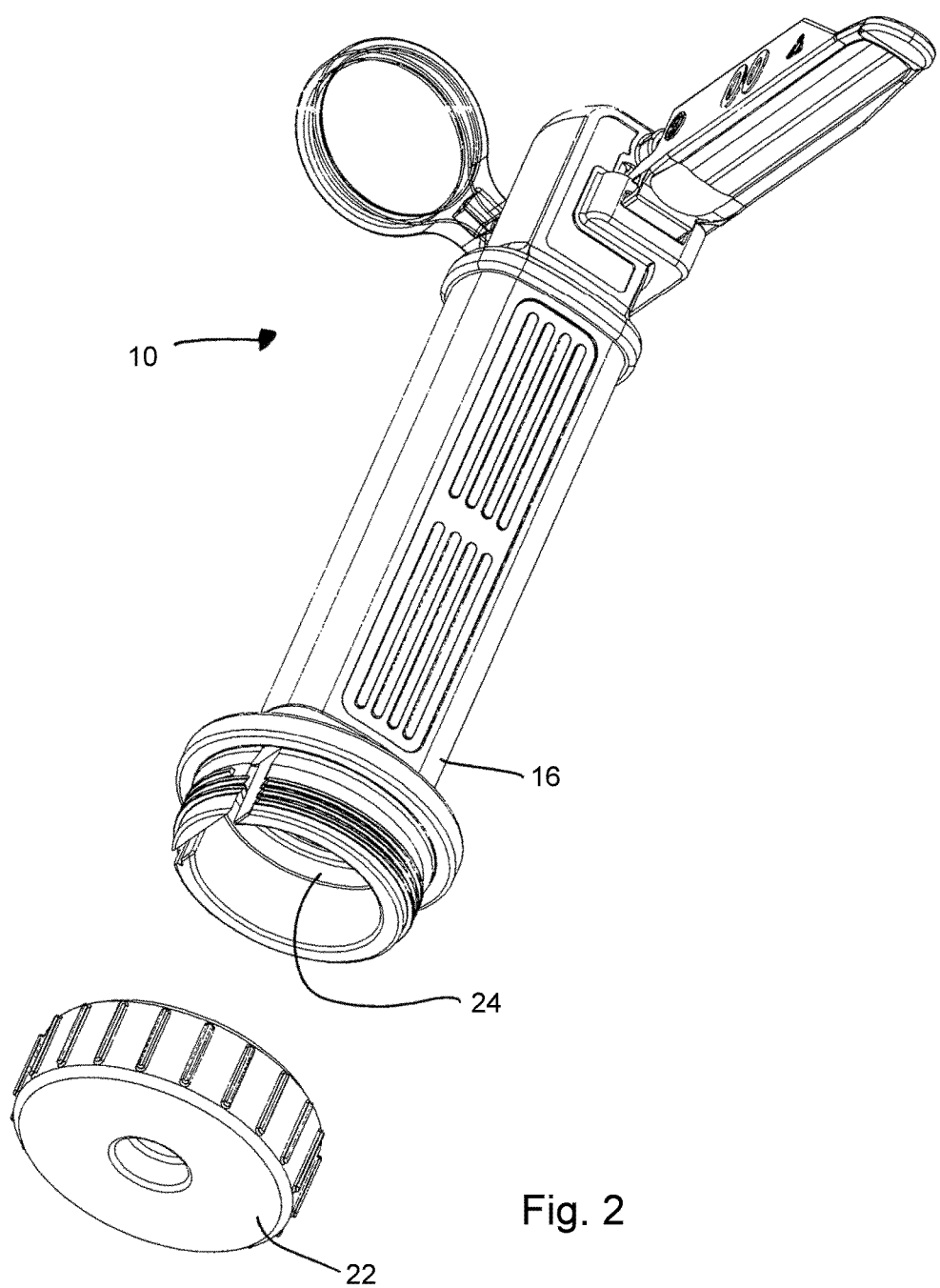
FIG. 2 is an exploded bottom perspective view of the laryngoscope illustrated in FIG. 1A.

As illustrated in FIG. 2, the grip comprises a cap 22 at a bottom end thereof. The cap 22 may be removable, for example screwably, providing access to a hollow interior 24 thereof. The interior 24 may be configured for receiving therein a battery, such as a standard dry cell. Accordingly, besides the interior 24 being shaped to receive and retain the battery, it may comprise necessary conductive elements (not illustrated) to electrically connect it to the functional portion 18 of the handle 12. Thus, the interior 24 may constitute a battery compartment of the laryngoscope 10.

According to some examples, the cap 22 itself is designed so as to receive therein a battery, such as a coin cell battery, with necessary conductive elements provided within the grip 16. According to these examples, the grip 16 need not comprise a hollow interior 24 as described above. However, it may be provided in order to allow for the conductive elements to be easily fitted within the grip 16.

Figure 3:
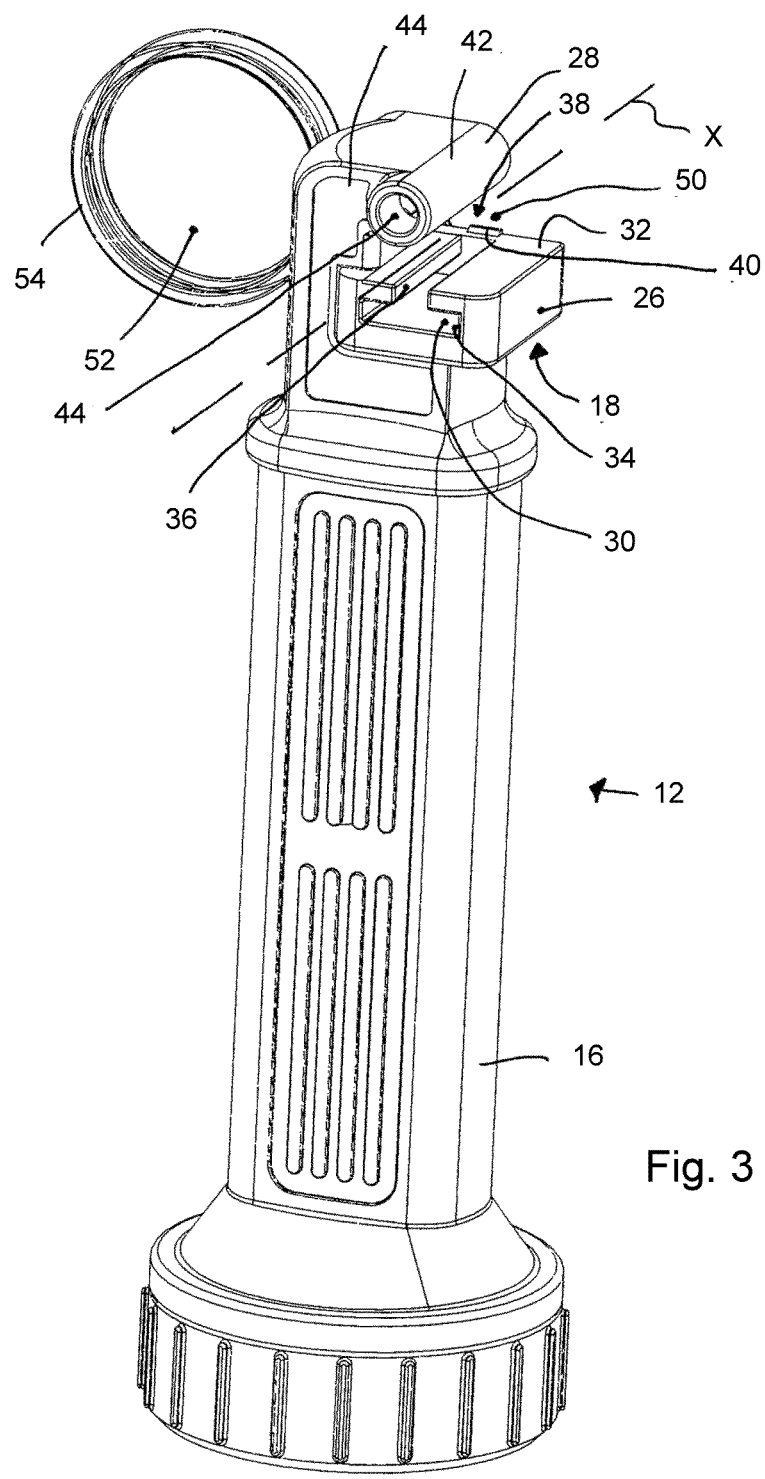
FIG. 3 is a perspective view of a laryngoscope handle of the laryngoscope illustrated in FIG. 1A.

As best seen in FIG. 3, the functional portion 18 of the handle 12 is associated with a viewing axis X, and comprises a blade-retention portion 26, which is configured slidingly receiving therewithin the blade 14, and a light source 28, which is configured to illuminate the blade, in particular a distal end 14b thereof.

As mentioned, the blade-retention portion 26 is configured to slidingly receive the blade 14 therewithin. To facilitate this, it comprises a slot 30 extending parallel to the viewing axis X. The slot 30 may be open to an upper surface 32 of the blade-retention portion 26, and comprise a primary channel 34 spaced from and substantially parallel to the upper surface, and a secondary channel 36 open to the surface and spanning between it and the primary channel, such that the primary channel projects toward both sides of the secondary channel (i.e., an inverted T-shape).

It will be appreciated that although the slot 30 as illustrated herein is open to the upper surface 32 of the blade-retention portion 26, the handle 12 may be designed such that the slot opens to another surface of the blade-retention portion, such as a side surface, or is only open toward a front side thereof.

A securing arrangement 38, configured to retain the blade when inserted therein, may be provided. According to one example, the securing arrangement 38 may comprise a ridge 40 projecting upwardly from the upper surface 32 of the blade-retention portion 26, immediately behind the slot 30, being arranged perpendicularly to the direction of insertion, i.e., to the viewing axis X. A suitable corresponding feature, such as a longitudinal indentation or lip, is formed on the blade 14 to cooperate with the securing arrangement 38.

The securing arrangement 38 may be provided according to any other suitable design, mutatis mutandis. For example, it may comprise a longitudinal indentation or lip, with the corresponding feature on the blade 14 comprising a ridge as described above.

The securing arrangement 38 and corresponding feature on the blade 14 are designed such that the blade may be fully inserted into the slot 30 with a small amount of linear force, and removed by slightly raising the proximal end 14a of the blade. Thus, the blade 14 is retained within the slot 30 during use, but may be easily inserted and removed by a user when necessary.

Reverting to FIG. 3, the light source 28 is disposed so as to illuminate in a direction substantially parallel to the viewing axis X. It comprises a housing 42 extending longitudinally parallel to the viewing axis X, and a lens 44 located at a distal end 42a thereof and provided to focus the light. For example, the lens 44 may be configured to focus the light to within a range of 15°-20°. A lamp (not illustrated) is located within the housing 42, and arranged such that it directs its light toward the lens 44 (e.g., one or more reflective surfaces may be provided for this purpose). The lamp may be any suitable element, such as a light-emitting diode (LED), an incandescent bulb, etc. According to some examples, the lamp and lens may be provided as a single unit (e.g., an LED within an encapsulation dome lens), or the lens may not be provided.

Power for the light source 28 may be provided by one or more batteries received within the interior 24 of the grip 16, as described above with reference to FIG. 2. Accordingly, an arm 46 connecting between the light source 28 and the blade-retention portion 26 is provided, in which one or more electrical connections (e.g., wires and the like) between the interior 24 of the grip 16 and the light source 28, in particular the lamp thereof. The arm 46 further functions to position the light source 28 over the blade-retention portion 26. In addition, a switch 48 (not illustrated in FIG. 1A), configured to control operation of the light source 28, may be provided.

Reverting to FIGS. 1A and 1B, the position of the light source 28 above the blade-retention portion 26 allows for the light source to be illuminate along a top surface of the blade 12. According to some examples, for example as illustrated in FIG. 1B, the blade may be made of a transparent material, and designed such that when received within the slot, its proximal end 14a is substantially in front of and facing the light source 28. According to this design, the blade 14 constitutes a light guide, transporting light emitted by the light source 28 to the distal end 14b thereof, thereby obviating the need to provide a blade having a dedicated light source.

As can be seen, for example in FIG. 3, the functional portion 18 is designed to provide visual access to a user along the entire length of the blade 14, when looking from its proximal end 14a. Thus, the user is afforded a view parallel to the blade 14 (and the viewing axis X). This may be useful, e.g., for use with small patients such as infants, and particularly neonates. In order to facilitate this, an area 50, or a majority thereof, above the blade-retention portion 26 and/or the slot 30, and surrounding the light source 28 (e.g., to one side, i.e., right or left, thereof), is substantially free of visual obstructions along the viewing axis X.

It will be appreciated that providing a slot 30 which allows for insertion of the blade 14 in a direction which is substantially parallel to the viewing axis X, allows for a design wherein the area 50 above the blade is substantially free of material of the handle, thereby facilitating providing such an area which is free of visual obstructions as described above.

As the design of the functional portion 18 provides visual access along the viewing axis X along the entire length of the blade 14, one or more viewing aids may be provided on the viewing axis. For example, a magnifying glass 52 may be provided, configured to be selectively disposed behind the area 50, i.e., along the viewing axis X.

The magnifying glass 52 may be mounted within a frame 54 which is rotationally articulated to either the grip 16 or the functional portion 18 of the handle 12. This arrangement enables the user to selectively move the magnifying glass into and out of the field of view along the viewing axis X.

Figure 4:
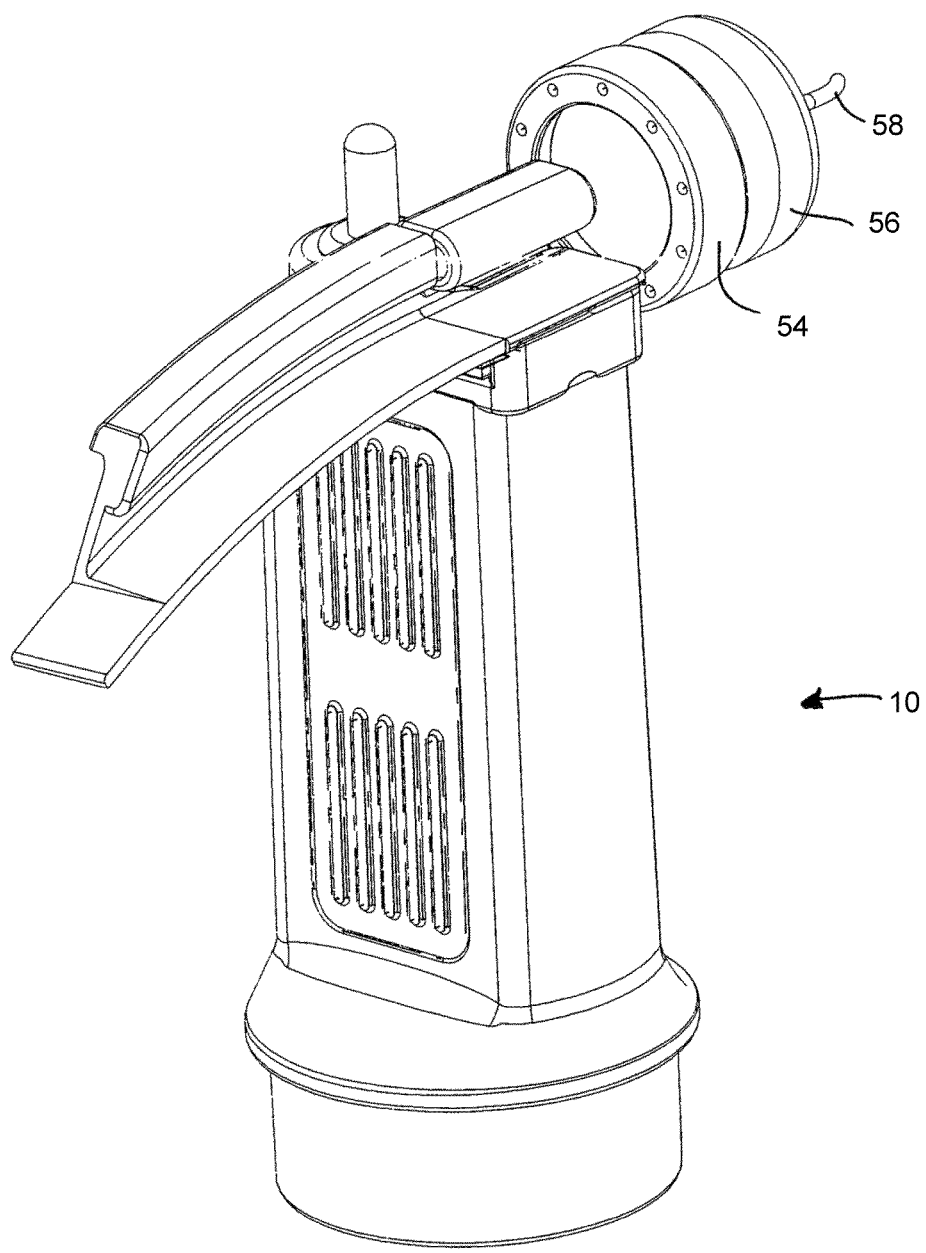
FIG. 4 is a perspective view of the laryngoscope illustrated in FIG. 1B with a camera.

Alternatively or in addition thereto, as illustrated in FIG. 4, a camera 56 may be provided, mounted to the frame 54. The camera 56 may be configured to capture still images and/or video. It may be attached view a wired connection 58 as shown, or wirelessly, according to any suitable protocol, many of which are well known in the art. The camera 56 may be configured to be used in conjunction with the magnifying glass 52, or without it. Although only a camera mounted to the frame is described herein, it will be appreciated that, equivalently, a camera could be provided integrally to the handle or a retrofittable camera may be provided.

Figure 5B:
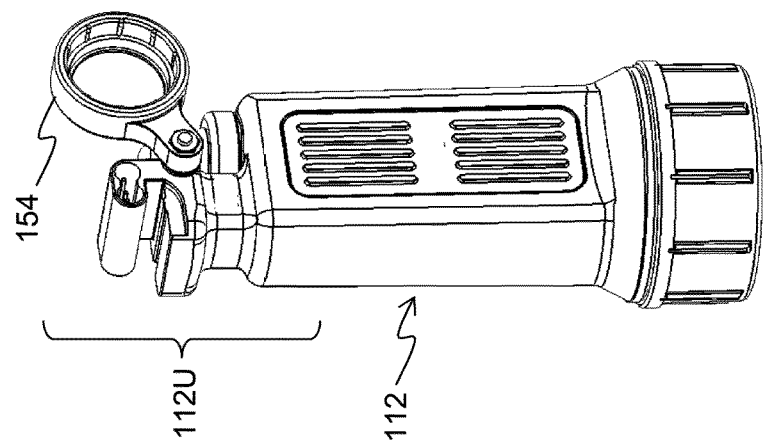
FIG. 5B is a reverse perspective view of a further example of laryngoscope handle according to the presently disclosed subject matter.
Figure 5A:
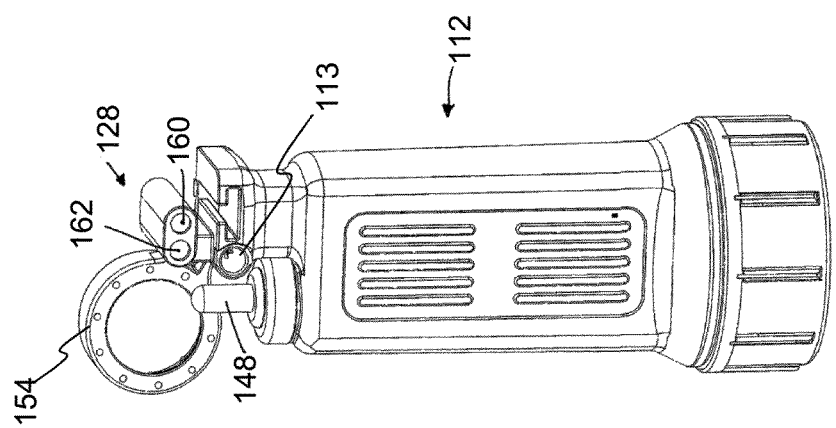
FIG. 5A is a perspective view of a further example of laryngoscope handle according to the presently disclosed subject matter.

As illustrated in FIGS. 5A and 5B, the light source 128 may comprise more than one lamp, e.g., a main lamp (located within the element indicated at 160; and an auxiliary lamp 162. The switch 148 may be configured to selectively turn on the main lamp 160 by itself, or both the main lamp and the auxiliary lamp 162 together. The auxiliary lamp 162 may be useful, for example, to supplement the main lamp 160 to facilitate the handle's 112 use for transillumination (e.g., without the blade 14).

Figure 5D:
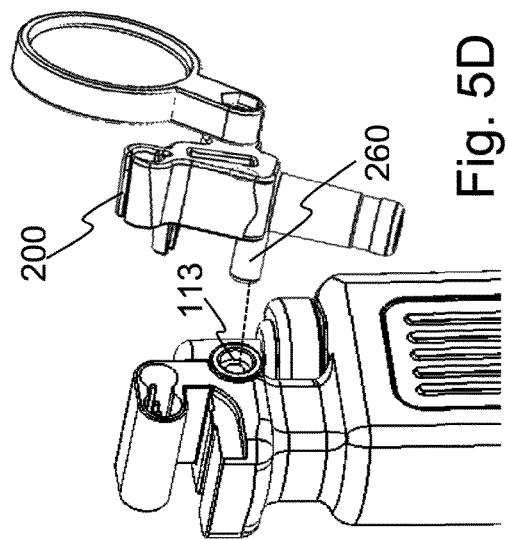
FIG. 5D is a further view of the upper section of an example of a laryngoscope handle and a retrofittable insufflation module which may be coupled thereto.
Figure 5C:
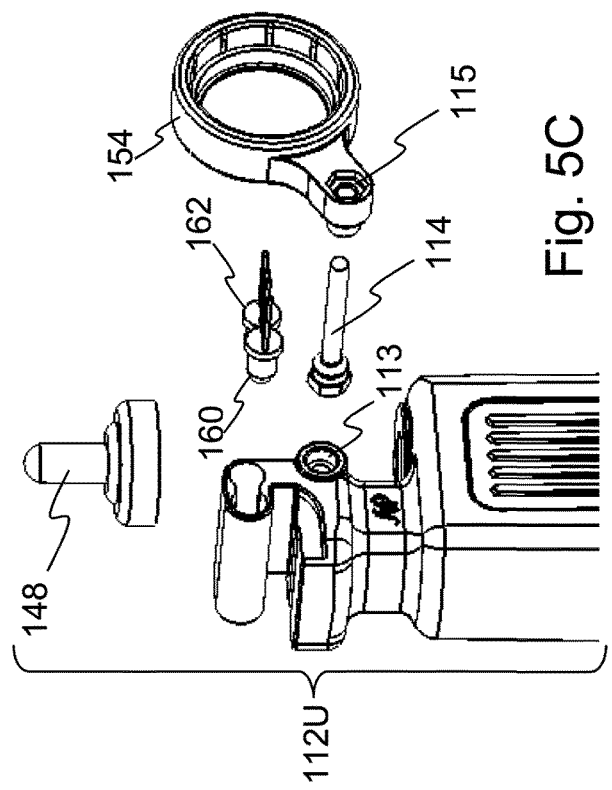
FIG. 5C is an exploded view of the upper section of an example of a laryngoscope handle according to the presently disclosed subject matter.

Reference is now made to FIG. 5C which is a schematic exploded view of the upper portion 112U of the handle 112 indicating how a lens mount 154 may be coupled to the handle 112 via a coupling mechanism including a handle socket 113, a coupling pin 114 and a lens mount socket 115.

It will be appreciated that the handle socket may be further utilized to attach other extension modules to the handle 112, thereby extending the functionality of the laryngoscope. For example a viewing aid such as a retrofittable camera extension or a magnifying lens may be provided. Additionally or alternatively, a camera may be provided having dimensions selected so as to be suitable for replacing at least one of the lamps 160, 162. Further for example, as illustrated in FIG. 5D, a retrofittable insufflation module 200, such as described in further detail herein, may be coupled to the handle socket 113 via a coupling pin 260.

Figure 6:
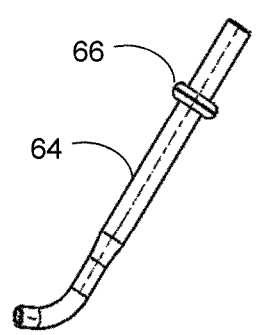
FIG. 6 is an isometric view of intubation guide according to the presently disclosed subject matter.
Figure 7:
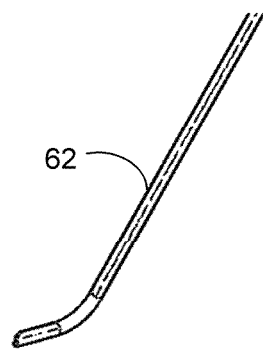
FIG. 7 is an isometric view of a catheter for use with the intubation guide illustrated in FIG. 6.
Figure 8:
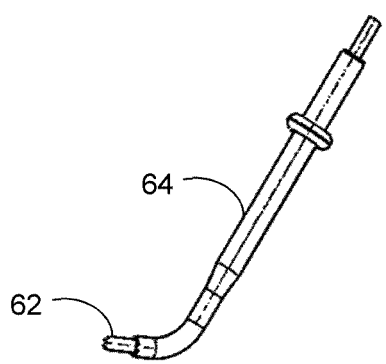
FIG. 8 is an isometric view of the catheter illustrated in FIG. 6 inserted into the intubation guide illustrated in FIG. 7.

As illustrated in FIGS. 6 through 8, a catheter 62 and a guide 64 may be provided. The catheter 62 may be used for different procedures, for example injection of surfactant materials into the lungs of neonates. The catheter 62 may be made of a flexible plastic material such as PVC, such that it can't be intubated without a guide such as a stylet. The guide 64 may have a "J"-shaped hollow tubular body, made from rigid plastic material, such as polypropylene. The guide 64 may comprise, at an upper part thereof, a bulge 66 providing a user with a place to grip during intubation and fixation of the guide 64 in the mouth, for example after intubation.

Typically, before intubation, the catheter 62 is inserted into the guide 64, as illustrated in FIG. 8, so that its distal end 62*a* protrudes by about 4-6 mm. This imparts appropriate stiffness and shape for intubation.

After intubation, the guide 64 may be fixed in the patient's mouth with help of adhesive tape, thereby mitigating the risk of spontaneous extubation. The intubation may be conducted with help of the laryngoscope as described above with reference to FIGS. 1 through 5, and/or with any other suitable laryngoscope.

Figure 9:
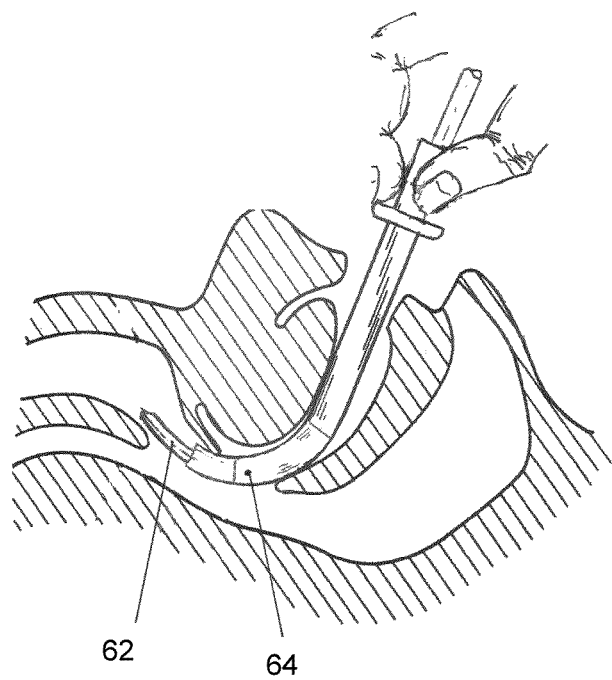
FIG. 9 is a pictorial view of the guide with the catheter inserted therein, as illustrated in FIG. 8, in a patient's mouth.

As illustrated in FIG. 9, during intubation, the catheter 62 or an endotracheal tube (not illustrated) is placed into the guide 64. The assembly is then inserted into patient's mouth and moved together with the guide 64 down the patient's throat until reaching the tracheal opening. The laryngoscope blade (not illustrated in FIG. 9) moves the tongue and presses the epiglottis before intubation of the tube, thereby facilitating passage.

Reference is now made to FIG. 10A which schematically represents an embodiment of an insufflation module 200 for providing insufflation functionality to a laryngoscope.

The insufflation module may be used in combination with a ventilator or a resuscitator system such as described in the applicants copending U.S. patent application Ser. No. 15/312,653 which is hereby incorporated by reference hererin, for example to stimulate breathing in neonatal patients.

The ventilator-resuscitator system comprises a ventilator-resuscitator device configured to provide a pressurized gas (e.g., an oxygen-air mixture; herein, the terms "gas", "gas mixture", "oxygen-air mixture", and similar terms, used alone or with one or more qualifiers such as "pressurized", are used interchangeably, unless otherwise clear from context, and should not be construed to limit the disclosure and/or claims). The ventilator may be connected by the insufflation module via a flexible tube such that pressurized gas from the ventilator may be delivered to a patient.

Jet insufflation allows oxygen or gas mixtures to be delivered into the intraoral cavity. The insufflation module 200 of the laryngoscope allows the jet to be directed along the laryngoscope blade to provide a desired concentration of oxygen or required gas mixtures within the intraoral cavity and the trachea to reduce the risk of hypoxia during prolonged intubation.

Furthermore, it has surprisingly been found that the use of jet insufflation can reduce the vapor content of the injected gas mixture within cavity thereby preventing fogging and improving visibility particularly during video laryngoscopy.

The insufflation module 200 includes a body 210, a jet nozzle 220, an inlet pipe connector 270, a gas inlet 272, a laryngoscope-coupling mechanism 260 and a auxiliary tube attachment dock 280.

The jet nozzle 220 extends from the body 210 of the insufflation module 200. When the insufflation module 200 is connected to a laryngoscope handle, the jet nozzle 220 is configured to deliver a high velocity stream of gas in a direction substantially along a blade of the laryngoscope such that the gas is deliverable into an intraoral cavity.

The inlet pipe connector 270 includes a narrow waist 274 for anchoring a flexible gas delivery pipe to the insufflation module 200 such that gas is delivered to the gas inlet 272.

Figure 12:
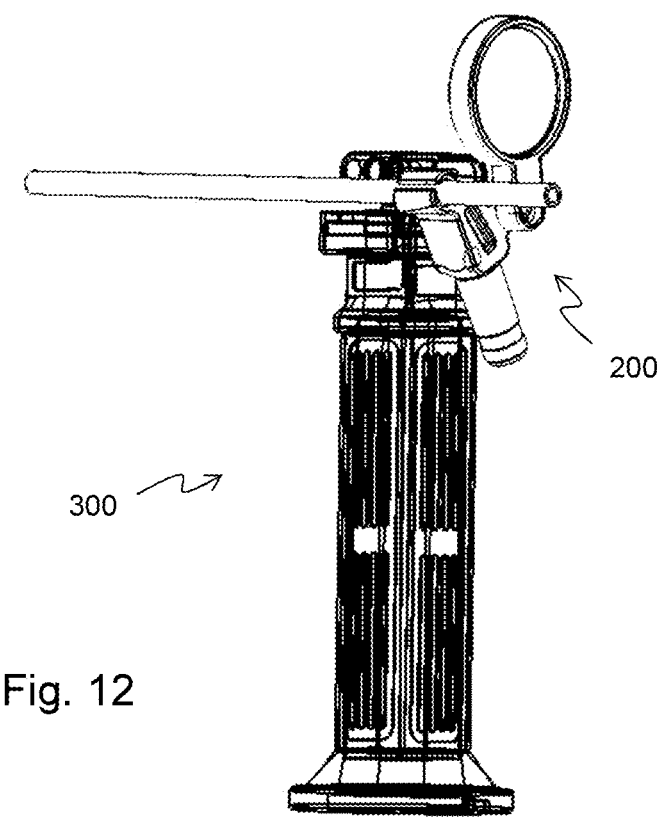
FIG. 12 represents the retrofittable insufflation module attached to the laryngoscope handle.

The laryngoscope-coupling mechanism 260 may be used to secure the insufflation module 200 to a laryngoscope handle 300 such as indicated in FIG. 12. With reference to FIG. 13B, the laryngoscope-coupling mechanism 260 may be configured to engage a corresponding module-coupling mechanism 313 of a laryngoscope handle 300 such that the insufflation module 200 is securely fastened thereto.

With reference to FIG. 10B and FIG. 10C, the insufflation module 200 may further be configured to bear a lens mount 254 for carrying a a magnifying lens to be used with the laryngoscope.

Referring particularly to FIG. 10C showing an exploded view of the retrofittable insufflation module 200 and the lens mount 254, it is noted that the insufflation module 200 may further include a module-coupling mechanism 213. The module-coupling mechanism 213, such as a socket, dock, clip or the like, may be used to engage a coupling pin of a retrofittable extension module such as the lens mount 254. It will be appreciated that in other embodiments, other module extensions may be connected using the module-coupling mechanism 213.

In still other embodiments, the module-coupling mechanism may itself comprise a coupling pin configured to engage a corresponding socket of a retrofittable extension module. Indeed further engagement mechanisms will occur to those skilled in the art.

It is particularly noted that where appropriate, the module-coupling mechanism, such as a round socket or the like may be configured to securely engage a corresponding coupling mechanism such as a round connecting pin or the like. Accordingly, an extension module may be coupled to either the laryngoscope handle or to the insufflation module in such as a manner as to allow rotational movement around its central axis and to prevent lateral or longitudinal movement.

Figure 13A:
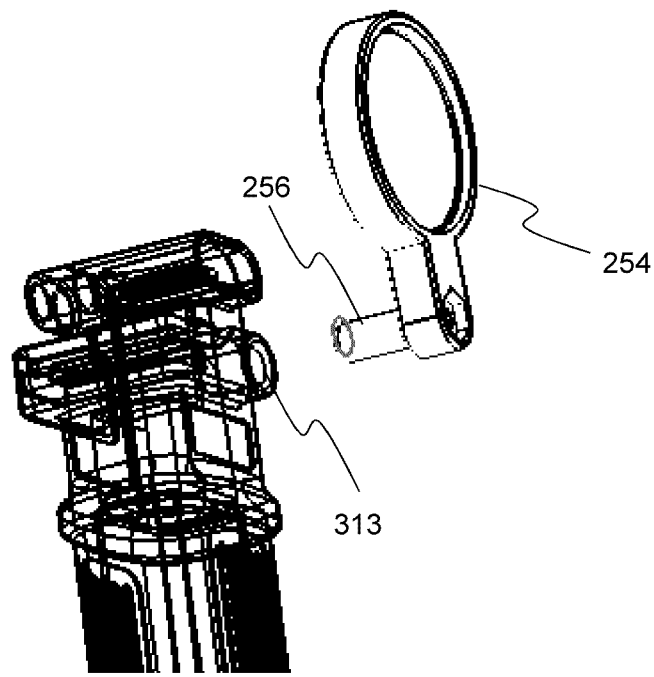
FIGS. 13A and 13B indicate how a common coupling socket may be used to couple the laryngoscope handle to either of a lens mount or an insufflation module as required.
Figure 13B:
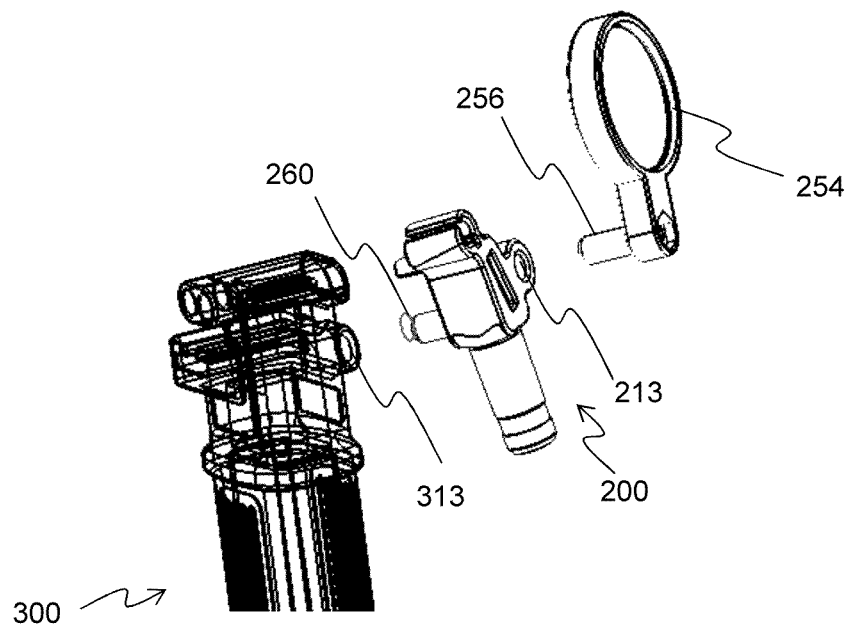

Referring now to FIGS. 13A and 13B it is particularly noted that, where appropriate, the module-coupling mechanism 213 of the insufflation module 200, may have similar dimensions to the module-coupling mechanism 313 of the laryngoscope handle 300. Accordingly, a lens mount 254

Figure 10D:
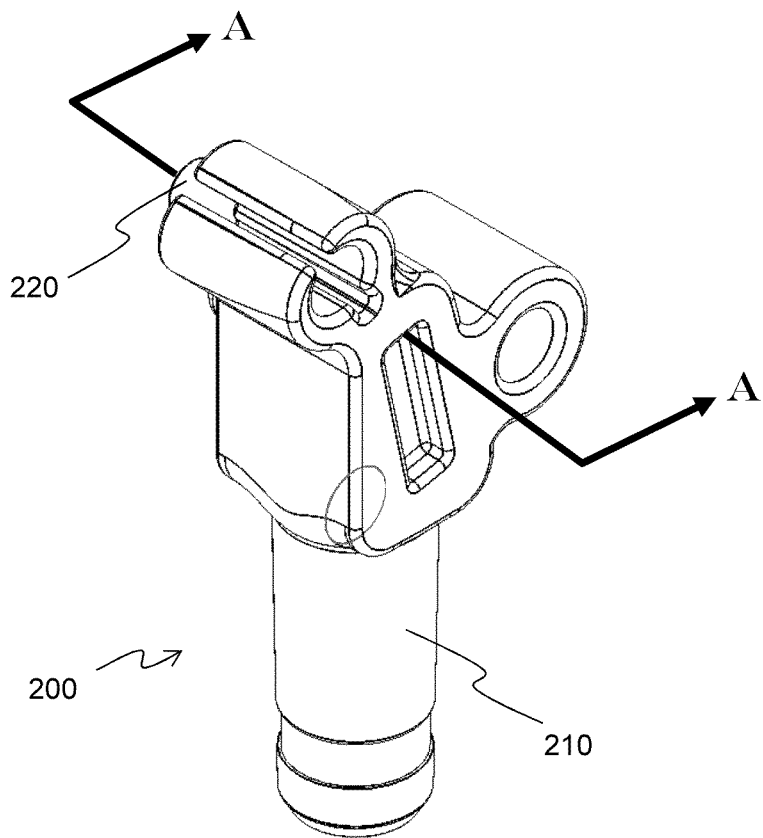
FIG. 10D and FIG. 10E are respectively a perspective view and a truncated cross-section of a retrofittable insufflation module for a laryngoscope handle according to the presently disclosed subject matter showing a central duct for delivering gas to a jet nozzle.
Figure 10E:
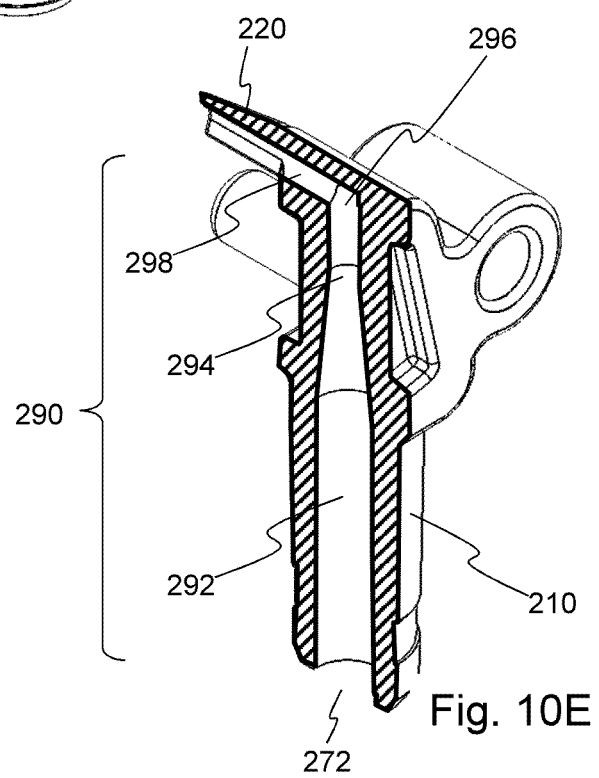

Reference is now made to FIG. 10D and FIG. 10E. FIG. 10D represents a perspective view of the retrofittable insufflation module 200 and FIG. 10E represents a truncated cross-section of the same insufflation module 200 along the line and in the direction indicated by A-A.

The cross section shows the central duct 290 therewithin for delivering gas to the jet nozzle 220. The gas duct 290 extends from the gas inlet 272 to said jet nozzle 220 through the body of the insufflation module 210.

The gas duct 290 includes a neck portion 292, a throat portion 264 and a bend 296. The neck portion 292 has a decreasing cross section tapering towards the throat portion. Accordingly, when a pressurized gas stream is introduced via the gas inlet 272 the flow-rate of the gas stream increases as the gas flows through the duct 290. The throat portion 294 receives the gas streams and directs it around the bend 296 towards a narrow opening of the jet nozzle 220 such that the gas stream issues from the jet nozzle 220 at a high velocity;

It is particularly noted that the bend 296 in the gas duct 290 may be a sharp angle of say 90 degrees or so. For example bends within the range of 80 to 100 degrees may enable the gas to be conveniently delivered.

Figure 11:
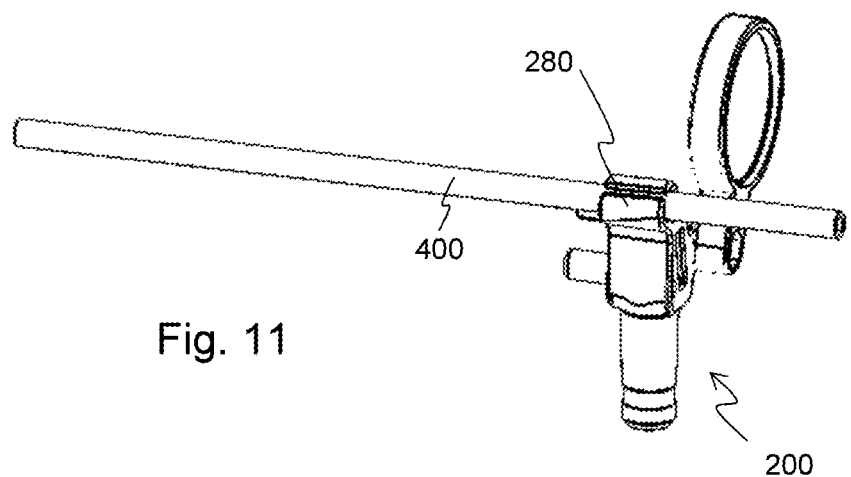
FIG. 11 is still another view of the retrofittable insufflation module further having an auxiliary tube attachment coupled thereto.

Referring now to FIG. 11, showing another view of the retrofittable insufflation module 300 further having an auxiliary tube 400 attachment coupled thereto via the attachment dock 290 provided for the purpose. The auxiliary tube attachment dock 290 is a clamping member or clip configured to secure an auxiliary tube 400 in such a way as to allow the auxiliary tube 400 to extend along the line of a laryngoscope blade.

The auxiliary tube may be used variously, for example to provide suction during intubation or to guide an auxiliary catheter into a vocal cord in order to administer surfactant to an infant in the case of respiratory distress syndrome.

Those skilled in the art to which this invention pertains will readily appreciate that numerous changes, variations and modifications can be made without departing from the scope of the invention mutatis mutandis.

Technical and scientific terms used herein should have the same meaning as commonly understood by one of ordinary skill in the art to which the disclosure pertains. Nevertheless, it is expected that during the life of a patent maturing from this application many relevant systems and methods will be developed. Accordingly, the scope of the terms such as computing unit, network, display, memory, server and the like are intended to include all such new technologies a priori.

As used herein the term "about" refers to at least ±10%.

The terms "comprises", "comprising", "includes", "including", "having" and their conjugates mean "including but not limited to" and indicate that the components listed are included, but not generally to the exclusion of other components. Such terms encompass the terms "consisting of" and "consisting essentially of".

The phrase "consisting essentially of" means that the composition or method may include additional ingredients and/or steps, but only if the additional ingredients and/or steps do not materially alter the basic and novel characteristics of the composition or method.

As used herein, the singular form "a", "an" and "the" may include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments or to exclude the incorporation of features from other embodiments.

The word "optionally" is used herein to mean "is provided in some embodiments and not provided in other embodiments". Any particular embodiment of the disclosure may include a plurality of "optional" features unless such features conflict.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween. It should be understood, therefore, that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6 as well as non-integral intermediate values. This applies regardless of the breadth of the range.

It is appreciated that certain features of the disclosure, which are, for clarity, described in the context of separate embodiments, may also be provided in combination in a single embodiment. Conversely, various features of the disclosure, which are, for brevity, described in the context of a single embodiment, may also be provided separately or in any suitable subcombination or as suitable in any other described embodiment of the disclosure. Certain features described in the context of various embodiments are not to be considered essential features of those embodiments, unless the embodiment is inoperative without those elements.

Although the disclosure has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the disclosure.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present disclosure. To the extent that section headings are used, they should not be construed as necessarily limiting.

What is claimed is:

1. An insufflation module for providing insufflation functionality to a laryngoscope said insufflation module comprising:
    a body;
    a jet nozzle extending from said body, said jet nozzle configured and operable to deliver a high velocity stream of gas in a direction substantially along a blade of the laryngoscope such that the gas is deliverable into an intraoral cavity;
    an inlet pipe connector configured to connect said body to a gas delivery pipe;
    a gas inlet via which said gas may be introduced; and
    a gas duct extending from said gas inlet to said jet nozzle through the body of the insufflation module, said gas duct comprising a neck portion and a throat portion,
        said neck portion comprising a decreasing cross section tapering towards the throat portion such that when a pressurized gas stream is introduced via the gas inlet the flow-rate of the gas stream increases as the gas stream flows through the duct, and
        said throat portion terminating in a narrow opening of the nozzle such that the gas stream issues from the jet nozzle at a high velocity;
    wherein
        said insufflation module further comprises a laryngoscope-coupling mechanism configured to engage with a corresponding module-coupling mechanism of a laryngoscope such that the insufflation module is securely fastened thereto.

2. The insufflation module of claim 1 wherein said laryngoscope coupling mechanism comprises a coupling pin and said corresponding module-coupling mechanism comprises a socket configured to rotatably engage said coupling pin.

3. The insufflation module of claim 1 said body further comprising at least one additional module coupling mechanism for connecting further modules thereto.

4. The insufflation module of claim 2 wherein said corresponding module coupling mechanism comprises a lens-mount coupling mechanism comprising a socket configured to rotatably engage a coupling pin of a lens-mount.

5. The insufflation module of claim 3 wherein said additional module-coupling mechanism has similar dimensions to said corresponding module-coupling mechanism of said laryngoscope.

6. The insufflation module of claim 1 further comprising an auxiliary tube attachment dock configured to secure an auxiliary tube such that said auxiliary tube extends along the laryngoscope blade.

7. The insufflation module of claim 1 further comprising an auxiliary tube extending along the laryngoscope blade.

8. The insufflation module of claim 1 further comprising a magnifying lens alignable along a viewing axis of said laryngoscope.

9. The insufflation module of claim 1 wherein said throat portion of said gas duct comprises a bend directing said gas stream towards said jet nozzle.

10. The insufflation module of claim 9 wherein said bend has an angle within the range 80 and 100 degrees.

11. The insufflation module of claim 1 wherein said inlet pipe connector comprises a narrow waist configured to anchor a flexible pipe secured thereby.

* * * * *